United States Patent
Beattie

[19]

[11] Patent Number: 6,156,502
[45] Date of Patent: *Dec. 5, 2000

[54] ARBITRARY SEQUENCE OLIGONUCLEOTIDE FINGERPRINTING

[76] Inventor: Kenneth Loren Beattie, 2 Hollymead Dr., The Woodlands, Tex. 77381

[ * ] Notice: This patent issued on a continued prosecution application filed under 37 CFR 1.53(d), and is subject to the twenty year patent term provisions of 35 U.S.C. 154(a)(2).

[21] Appl. No.: 08/769,651

[22] Filed: Dec. 19, 1996

Related U.S. Application Data

[60] Provisional application No. 60/009,027, Dec. 21, 1995, abandoned.

[51] Int. Cl.$^7$ .............................. C12Q 1/68; C12P 19/34; C07H 21/04
[52] U.S. Cl. ..................... 435/6; 435/91.2; 435/91.21; 435/91.5; 435/91.51; 435/5; 536/24.3; 536/24.31; 536/24.32; 536/24.33
[58] Field of Search .................... 935/7, 77, 78; 435/4, 5, 6, 91.2, 91.5, 91.21, 91.51; 536/22.1, 23.1, 24.3, 24.33, 24.31, 24.32

[56] References Cited

U.S. PATENT DOCUMENTS

| | | | |
|---|---|---|---|
| 5,204,100 | 4/1993 | Carozzi et al. | 424/93 |
| 5,487,985 | 1/1996 | McClelland et al. | 435/91.2 |
| 5,700,637 | 12/1997 | Southern | 435/6 |
| 5,962,221 | 10/1999 | Cactano-Anolles | 435/6 |

OTHER PUBLICATIONS

Beattie et. al. Clin. Chem. 41:700–706 (May 1995).
Welsh et al. Nucl. Ac. Res. 18:7213–7218 (Dec. 1990).
Williams Biotechniques 7:762–768 (1989).
Khrapko et al. FEBS Lett. 256:118–122 (Oct. 1989).
Yershov et al. P.N.A.S., USA 93:4913–4918 (May 1996).
Southern et al. Genomics 13:1008–1017 (1992).
Nikiforov et al. Nuc. Ac. Res. 22:4167–4175 (Oct. 1994).
Lehrach et al. Genome Analysis. vol. 1: Genetic and Physical Mapping, 39–81, 1990.

*Primary Examiner*—Carla J. Myers
*Attorney, Agent, or Firm*—Benjamin Aaron Adler

[57] ABSTRACT

The present invention provides a method of arbitrary sequence oligonucleotide fingerprinting (ASOF), a novel technology which eliminates gel electrophoresis as a step in polymorphic marker analysis, species identification and transcriptional profiling. ASOF greatly increases the speed and throughput of analysis, with aconcomitant decrease in cost. Furthermore, the miniaturization and automation of ASOF analysis leads to an exceedingly increased throughput of nucleic acid analysis.

19 Claims, 6 Drawing Sheets

CF01/I (5-26) - box 15-16

CF01/I (5-26) - box 9-10

CF01/I (5-24) - box 15-16

CF01/I (5-24) - box 9-10

CF02/I - box 15-16

CF02/I - box 9-10

UK/I - box 15-16

UK/I - box 9-10

ARBITRARY SEQUENCE OLIGONUCLEOTIDE FINGERPRINTING

CROSS REFERENCE TO RELATED APPLICATION

The present application claims priority to provisional application U.S. Ser. No. 60/009,027, filed Dec. 21, 1995, now abandoned.

BACKGROUND OF THE INVENTION

1. Field of the Invention

The present invention relates generally to the fields of molecular biology and nucleic acid analysis. More specifically, the present invention relates to a novel method of genetic analysis using arbitrary sequence oligonucleotide fingerprinting.

2. Description of the Related Art

A certain amount of DNA sequence variation occurs naturally within a population of individuals. At many chromosomal positions, the frequency of sequence variation within a population is great enough to yield useful DNA markers, and the occurrence of a polymorphic allele at a frequency of about 10% is generally considered useful for mapping purposes (1). Analysis of DNA polymorphisms has been extremely valuable for identifying genetic markers tightly linked to genes associated with phenotypic traits. The use of gel electrophoresis to detect restriction fragment length polymorphism (RFLP) has yielded thousands of mapped polymorphic DNA markers in various species. The most frequent type of genetic change associated with an RFLP marker is point mutation within the recognition sequence of a restriction enzyme.

Although restriction fragment length polymorphism analysis remains a widely used method for detecting DNA sequence polymorphism, several useful variations on the fragment length theme have recently been introduced. The existence of variable number tandem repeat (VNTR) or "microsatellite" sequences scattered throughout genomic DNA has been exploited in the identification of polymorphic markers (2,3). Micro-satellite probes have been used to detect polymorphisms in length of restriction fragments (2) and PCR products (3). Variable length "short tandem repeats" (STRs) such as (CA)n are highly polymorphic and serve as informative markers (4,5).

Another recent advance in polymorphic marker analysis is single short primer PCR, or "random amplified polymorphic DNA" (RAPD) marker analysis. Conduct of PCR with genomic DNA using single short (8–10 mer) primers of arbitrary sequence generates a product that can be used in gel electrophoretic fingerprint analysis to generate numerous polymorphic markers (6,7). Although variable number tandem repeat markers, short tandem repeats and RAPD markers have significantly increased the rate of polymorphic marker discovery and the throughput of polymorphic marker analysis, their analysis is limited by the requirement of labor intensive gel electrophoresis, which typically requires several hours of time and accommodates a relatively small number of tests at one time (less than 100).

Microbial identification is another analytical task that benefits from the present invention. Identification of bacterial, viral and mycotic species, strains and subtypes is a key concern in clinical microbiology, for diagnosis of infectious disease, selection of effective pharmaceutical treatment, and epidemiological investigation of the source and spreading of infectious disease. Microbial identification is also a vital capability in the detection and management of biological warfare agents. Microbial identification is also important in, agricultural, industrial and environmental biomonitoring, for example in the detection of pathogens that reduce agricultural productivity as well as microbes that put nutrients into the soil, in the monitoring of industrial bioprocesses, and in the assessment of biodegradation capacity in soil and waste treatment facilities. Microbial identification typically involves time consuming and expensive culturing and biochemical procedures, as well as costly and complex immunological tests. DNA sequencing and PCR analysis can also be performed to achieve accurate microbial identification and typing, but like current DNA typing procedures, these microbial DNA diagnostic tests require gel electrophoretic analysis, which is time consuming and labor intensive and accommodates a relatively low sample throughput. Analysis of microbial populations, important in environmental and industrial settings, is currently a daunting task, typically requiring extensive culturing and a battery of biochemical tests, supplemented by crude classification by visual inspection. Many of the microbial species in environmental samples are not readily culturable, making detection and identification extremely difficult.

Analysis of gene expression is another area that benefits from the present invention. Transcriptional profiling, i.e., analysis of the relative abundance of messenger RNA transcribed from different genes, is critical to the understanding of patterns of gene expression that are associated with all biological processes, including development, differentiation, response to environmental stresses, and other cellular and organismal functions of interest to basic scientists. The ability to analyze patterns of gene expression can lead to discovery of new genes associated with biological processes. A detailed understanding of gene regulation at the transcriptional level is also a premier concern of the pharmaceutical industry, enabling identification of genetic targets for drug development and leading to the understanding of the well known heterogenity in the way different individuals respond to pharmaceutical interventions. Transcriptional profiling is currently conducted by the techniques of "differential display" (Liang, P. and Pardee, A. B. (1992) Science 257:967–971; Liang, et al., (1994) Nucl. Acids Res. 22:5763–5764; Prashar, Y. and Weissman, S. M. (1996) Proc. Nat'l. Acad. Sci., U.S.A. 93:659–663.) and "representational difference analysis" (Hubank, M. and Schatz, D. G. (1994) Nucl. Acids Res. 22:5640–5648; Lisitsyn, N. A. (1995) Trends Genet. 11:303–307), both of which involve PCR, gel electrophoretic analysis of DNA fragments, and a variety of other complex manipulations. A need clearly exists for new technology that enables more robust, rapid and cost effective quantitation of a very large number of gene transcripts.

The prior art is deficient in the lack of effective means for the rapid, simultaneous analysis of a large number of DNA markers, for rapid identification of species, strains, and sub-types and gender, and for rapid transcriptional profiling. The present invention fulfills this longstanding need and desire in the art.

SUMMARY OF THE INVENTION

The arbitrary sequence oligonucleotide fingerprinting technique of the present invention replaces gel electrophoresis with hybridization to a miniature array of numerous oligonucleotide probes, and enables simultaneous analysis of hundreds or thousands of DNA markers. DNA sequence polymorphisms (DNA markers) are important tools in genetic analysis, serving as genetic markers in agricultural breeding programs, facilitating the discovery of genes associated with genetic diseases or other traits, documenting the identity of individual humans, animals or plants, and indicating the extent of genetic diversity among populations. The present invention discloses an improved procedure for DNA marker analysis and other forms of nucleic acid sequence analysis, termed "arbitrary sequence oligonucleotide fingerprinting" (ASOF), which enables the rapid, simultaneous analysis of a large number of DNA markers. The expected high information content of arbitrary sequence oligonucleotide fingerprinting analysis facilitates many kinds of genetic analyses.

This invention provides an improved process for comparing nucleic acids extracted from different biological samples. One application of the invention is in the field of DNA marker analysis, wherein the identity of individuals is assessed through "DNA typing" (e.g., in forensic "identification"), and genes associated with specific phenotypic traits are identified and mapped to specific sites on the chromosomes. In the process of arbitrary sequence oligonucleotide fingerprinting, variations in the DNA sequence of different individuals of a species ("DNA sequence polymorphisms") are revealed by differences in the quantitative pattern of binding of DNA fragments prepared from different individuals to an array of a few hundred to a few thousand surface-tethered oligonucleotide probes of arbitrary nucleotide sequence.

The arbitrary sequence oligonucleotide fingerprinting technique of the present invention has important commercial application in several fields. For example, applications of the various embodiments of the technique of the present invention include DNA fingerprinting for individual identification—applied in forensic and paternity testing, DNA typing of prison and military populations, gender determination in plants and animals, genotyping of horses, cattle, poultry, wildlife species, proprietary plant cultivars, genetically engineered agricultural varieties, and eventually, household pets and every newborn child. Secondly, the techniques of the present invention allow simultaneous analysis of large numbers of DNA markers for, e..g, tracking down genes associated with genetic diseases or genes conferring susceptibility or resistance to infectious or genetic diseases or environmental stress, and for discovery of genes associated with desirable traits in plants and animals leading to commercial opportunities in medicine and agriculture. Thirdly, the techniques of the present invention allow profiling of gene expression (whereby hybridization pattern reflects relative abundance of different mRNA species), for example, to identify and isolate genes associated with biological responses of interest to the pharmaceutical industry. Fourthly, the techniques of the present invention allow assessment of genetic and/or biological diversity, e.g. addressing environmental concerns, and supporting the establishment of resources for discovery of new biotechnology products. Fifthly, the techniques of the present invention allow analysis of microbial population dynamics which is relevant to waste treatment, bioremediation and microbial and chemical process control. Finally, the techniques of the present invention allow microbial identification for infectious disease diagnostics and ecosystem surveillance.

A number of problems are solved by the present invention. Anticipated advantages of the genosensor-based arbitrary sequence oligonucleotide fingerprinting procedure over current gel electrophoresis-based DNA typing methods include: (1) greater speed of analysis; (2) higher throughput of analysis (ability to process larger numbers of samples per work day); (3) lower cost per analysis; (4) greater statistical reliability due to much higher information content; and (5) in some embodiments, direct analysis of complex nucleic acid sequences without the use of DNA amplification.

A key feature, common to all embodiments of the arbitrary sequence oligonucleotide fingerprinting technique of the present invention, is the use of a set of arbitrary sequence oligonucleotide probes, each sequence located at a specific site on a hybridization support via binding of the short strands to the surface at one end.

Another significant embodiment of the present invention is in the use of arbitrary sequence oligonucleotide arrays for gene expression profiling, which constitutes a strategy of "differential display on a chip." Bulk messenger RNA is extracted from cells, subjected to reverse transcription to form cDNA. PCR is then performed to generate subsets of expressed sequences, as in the prior art of differential display, and instead of displaying the PCR fragments by gel electrophoresis, in the present invention the PCR mixture is hybridized with an array of arbitrary sequence oligonucleotides to generate a hybridization fingerprint which quantitatively reflects the relative abundance of different mRNA species. The length of oligonucleotide probes arrayed across the genosensor chip can be adjusted to accommodate variations in total sequence complexity of the PCR fragments, as is done in the application of ASOF in polymorphic marker analysis, so that on average, each transcript hybridizes to one or a few sites across the array. Changes in gene expression will result in changes in the hybridization signal intensity at different positions across the genosensor array, and target sequences bound to the relevant sites can be released (melted off by hot water) for further analysis, including cloning and sequencing. In a preferred embodiment of the present invention for gene expression profiling, the array of arbitrary sequence oligonucleotide probes is formed in the "flowthrough genosensor" (Beattie, K. L. (1994) Microfabricated, Flowthrough Porous Apparatus for Discrete Detection of Binding Reactions, patent application PCT/US94/12282, filed Oct. 27, 1994; Beattie, et al., (1995) Clin. Chem. 41:700–706.), in which probes are immobilized within hybridization cells containing densely arrayed smooth channels or pores of 1–10 micron diameter, extending across a silicon or glass wafer typically 500 microns thick. Dilute nucleic acid solutions can be analyzed by flowing them through the porous glass hybridization array, and the quantity of bound material per unit cross section is on the order of 100 times that of the flat surface genosensor array, which greatly increases the sensitivity and dynamic range of the analysis. Also advantageous for transcriptional profiling using the present invention, the flowthrough genosensor configuration facilitates recovery of hybridized strands for further analysis.

The present invention can also be advantageously applied to the profiling of genomes and expressed genes from mixed populations of organisms, for example, microbial populations in soil samples and waste treatment facilities. By using arbitrary sequence probes of length appropriate for the total genetic complexity of the sample, a specific hybridization fingerprint may be produced from the environmental sample which reflects the microbial population, and a change in the microbial population can be seen as a change in the hybridization fingerprint.

Additional embodiments of the present invention are disclosed which enable direct hybridization fingerprinting of highly complex nucleic acid mixtures, without the necessity of preparing a subset of sequences by PCR. The total nucleic acid sample (genomic DNA or RNA of total genetic complexity millions or billions of bases) is extracted from cells or mixed populations, labeled, and hybridized to arrays of longer oligonucleotide probes (of length 12–18 bases) to generate a complex fingerprint reflecting representative sequences from the entire nucleic acid sample. Obviously, much longer hybridization times are required for the direct fingerprinting embodiment of arbitrary sequence oligonucleotide fingerprinting than in the embodiments that include preparation of a subset of sequences by PCR. The flowthrough genosensor configuration, which enables analysis of dilute nucleic acid samples flowed through the porous array, is therefore a preferred hybridization substrate for the direct fingerprinting of nucleic acid samples of high genetic complexity. The direct fingerprinting embodiment of the present invention is a particularly preferred strategy for analysis of microbial genomes and messenger RNA populations, where the total genetic complexity is typically on the order of millions of bases.

For direct analysis of nucleic acid samples of total genetic complexity in the billion base range, such as genomic DNA of higher eukaryotes or bulk messenger RNA extracted from complex mixtures of microorganisms, the following embodiment of the current invention is preferred. Arrays of up to several thousand arbitrary sequence "capture probes" of length 7–9 bases are prepared, preferably in a flowthrough (porous glass) hybridization support. The complex nucleic acid sample is then mixed with one or more labeled oligonucleotides (also of arbitrary sequence and length 7–9 bases) and hybridized to the array of capture probes. The hybridization is carried out at an ionic strength and temperature at which short duplex regions (7–9 base pairs) are unstable but longer duplex regions (14–18 base pairs) are stable. Under these conditions, it is known that the nucleic acid strands will stably hybridize to the oligonucleotide array only when the capture probe and the labeled probe hybridize to a target strand in a tandem fashion, that is, form a continuous stretch of base-stacked duplex of combined length (Khrapko, et al., (1991) DNA Sequence 1:375–388.), 14–18 base pairs in this embodiment of the present invention. In this way, the total effective length of the probe is long enough to produce a meaningful hybridization fingerprint of the entire complex nucleic acid. If shorter probes were used, essentially all of the probes would hybridize at multiple sites within the highly complex nucleic acid target, and a totally occupied, meaningless fingerprint would be produced.

The key requirement that is fulfilled by adjusting the effective probe length to "match" the total genetic complexity of the target is to produce hybridization fingerprints in which only a fraction (typically ¼ to ⅔) of the hybridization sites are occupied by hybridized strands, so that on average, only one target sequence is bound within each hybridization cell. In the tandem probe embodiment of the present invention, the frequency of occurrence of contiguously stacked capture/labeled probes hybridized to the target strand can be conveniently adjusted (to produce a meaningful fingerprint) by varying the number of labeled oligonucleotide probe sequences that are included in the hybridization mixture.

The information content of the hybridization fingerprint can be greatly enhanced by using mixtures of labeled probes bearing a variety of distinguishable fluorophores, to simultaneously create a multiplicity of distinct fingerprints in the same hybridization reaction.

Another useful feature of the tandem probe embodiment for fingerprinting of complex nucleic acids is that the combination of capture and labeled probes, hybridizing in tandem with the target strand, immediately defines a sequence of 14–18 bases, which can be used to create a primer for further analysis of bound strands by dideoxy sequencing or PCR.

In addition to using single short (9–10 mer) arbitrary sequence primers for amplification of a specific subset of the genome (prior to hybridization to the array of arbitrary sequence probes), the present invention also discloses the use of mixtures of longer PCR primers (e.g., 100 13 mers of arbitrary sequence), at higher temperature of annealing, to obtain a more reproducible amplified genomic subset.

In addition to using arbitrary sequence PCR, the present invention also discloses the use of mixtures of longer PCR primers directed to known regions spaced across the genome (e.g., multiple pairs of 20–30 mers) to amplify specific, known genomic regions. The products would then be hybridized to arrays of arbitrary sequence probes, to obtain fingerprints that reveal sequence polymorphisms within the known regions. Regardless of the method chosen to prepare the genomic fragments, the hybridization fingerprint will be specific and quantitative, such that even a two-fold change in relative hybridization signal, such as that associated with homozygous vs. heterozygous condition, can be distinguished. An important aspect of the invention is the stepwise process whereby the combination of PCR with arbitrary array hybridization is first used to discover new sequence polymorphisms, then the specific combinations of primers and probes that test the new polymorphisms are implemented in a directed fashion to simultaneously analyze hundreds to thousands of sequence polymorphisms. Another important point not taught by the prior art is that the reproducible hybridization pattern seen for a given set of PCR fragments and probes is not entirely due to perfectly base paired duplex regions (i.e., Watson-Crick pairing between oligonucleotide probes and target strands). Many of the hybridization signals will involve imperfectly paired duplexes, containing one or more base mismatches or even regions of tertiary structure. The existence of imperfect duplexes is also influenced by sequence polymorphism, and as long as the hybridization patterns are reproducible, it does not matter whether they represent perfect matches. The well known patent issued to Dr. Southern, for example, specifically refers to perfect hybrids.

In a seventh embodiment of the present invention, there is provided a method for direct genomic fingerprinting of DNA samples of high genetic complexity, comprising the steps of: extracting genomic DNA from a biological sample; adding at least one labeled oligonucleotide probe of arbitrary sequence to the extracted DNA and hybridizing the mixture with an array of arbitrary sequence capture probes, using conditions of temperature and ionic strength under which neither the labeled probe(s), nor capture probes alone will stably hybridize with the DNA target, but under which capture and labeled probes, when tandemly hybridized to a target strand to form a longer, contiguously base-stacked combined duplex region, will result in stable capture of the target strand; and comparing the hybridization fingerprint with genomic fingerprints obtained from different biological samples.

In an eighth embodiment of the present invention, there is provided a method for direct transcriptional profiling of nucleic acid samples of high genetic complexity, comprising the steps of: extracting messenger RNA from a biological sample; adding at least one labeled oligonucleotide probe of arbitrary sequence to the extracted RNA and hybridizing the mixture with an array of arbitrary sequence capture probes, using conditions of temperature and ionic strength under which neither the labeled probe(s), nor capture probes alone will stably hybridize with the RNA target, but under which capture and labeled probes, when tandemly hybridized to a target strand to form a longer, contiguously base-stacked combined duplex region, will result in stable capture of the RNA transcript; and comparing the hybridization fingerprint with RNA fingerprints obtained from different biological samples.

In a ninth embodiment of the present invention, there is provided a method for direct fingerprint analysis of nucleic acid samples of high genetic complexity, comprising the steps of: extracting DNA or RNA from a biological sample; adding at least one labeled oligonucleotide probe of arbitrary sequence to the extracted nucleic acid and hybridizing the mixture with an array of arbitrary sequence capture probes, using conditions of temperature and ionic strength under which neither the labeled probe(s), nor capture probes alone will stably hybridize with the target strands, but under which capture and labeled probes, when tandemly hybridized to a target strand to form a longer, contiguously base-stacked combined duplex region, will result in stable capture of the target strand; comparing the hybridization fingerprint with fingerprints obtained from different biological samples; eluting bound target strands from any desired hybridization cell in the array, preferably by applying hot water to the desired location in the array; and further analyzing the eluted strands by methods selected from the group consisting of cloning, PCR or dideoxy sequencing, using (if desired) the combined sequence of the capture and labeled probes to define a longer primer for amplification or dideoxy sequencing.

Thus, in accordance with the above-described advantages and desirable features of the invention, in one embodiment of the present invention, there is provided a method of detecting polymorphisms between samples of genomic DNA, comprising the steps of: amplifying a first subset of genomic DNA sequences by a polymerase chain reaction using one or more oligonucleotide primers of arbitrary sequence; labeling said first amplified subset of genomic DNA; combining said first amplified subset of genomic DNA with a two-dimensional array of surface-bound oligonucleotide probes under hybridizing conditions to form a first quantitative hybridization fingerprint for said first subset of genomic DNA sequences; amplifying a second subset of genomic DNA sequences by a polymerase chain reaction using said one or more oligonucleotide primers of arbitrary sequence; labeling said second amplified subset of genomic DNA; combining said second amplified subset of genomic DNA with said two-dimensional array of surface-bound oligonucleotide probes under hybridizing conditions to form a second quantitative hybridization fingerprint for said subset of genomic DNA sequences; comparing said first quantitative hybridization fingerprint to said second quantitative hybridization fingerprint; and detecting polymorphisms in said samples of genomic DNA by detecting differences between said first quantitative hybridization fingerprint and said first quantitative hybridization fingerprint.

In an additional embodiment of the present invention, there is provided a method of detecting polymorphisms in a genomic DNA sample, comprising the steps of: amplifying a first subset of genomic DNA sequences by a polymerase chain reaction using a multiplicity of defined sequence oligonucleotide primer pairs directed toward a corresponding multiplicity of known genomic regions; labeling said first amplified subset of genomic DNA; combining said first amplified subset of genomic DNA with a two-dimensional array of surface-bound oligonucleotide probes under hybridizing conditions to form a first quantitative hybridization fingerprint for said first subset of genomic DNA sequences; amplifying a second subset of genomic DNA sequences by a polymerase chain reaction using said multiplicity of defined sequence oligonucleotide primer pairs directed toward a corresponding multiplicity of known genomic regions; labeling said second amplified subset of genomic DNA; combining said second amplified subset of genomic DNA with said two-dimensional array of surface-bound oligonucleotide probes under hybridizing conditions to form a second quantitative hybridization fingerprint for said subset of genomic DNA sequences; comparing said first quantitative hybridization fingerprint to said second quantitative hybridization fingerprint; and detecting polymorphisms in said samples of genomic DNA by detecting differences between said first quantitative hybridization fingerprint and said first quantitative hybridization fingerprint.

In yet another embodiment of the present invention, there is provided a method for profiling of gene expression at the level of transcription, comprising the steps of: extracting RNA from a biological sample; conducting reverse transcriptase-arbitrary primer PCR to amplify subsets of expressed sequences; labeling said amplified subsets of expressed sequences; hybridizing the labeled, amplified subsets of expressed sequences with an array of oligonucleotide probes of arbitrary sequence to produce a quantitative hybridization fingerprint; and detecting differences in gene expression from comparing said quantitative hybridization fingerprint with quantitative hybridization fingerprints obtained from a other experiments performed previously for other biological samples.

In another aspect of the present invention, there is provided an improved method of preparing oligonucleotide arrays for use in hybridization analyses, comprising the steps of: chemically synthesizing a desired set of oligonucleotide probes using 3'-amino-C3 controlled pore glass support material to produce completed desired oligonucleotides; cleaving said completed desired oligonucleotides from said support material in concentrated ammonium hydroxide to yield oligonucleotides bearing aminopropanol groups at their 3'-termini; cleaning a glass or silicon dioxide surface with organic solvents and drying at elevated temperature; applying a quantity of oligonucleotides bearing aminopropanol groups at their 3'-termini in aqueous solution to said surface of said clean, dry glass or silicon dioxide; allowing covalent bonding of said oligonucleotides bearing aminopropanol groups at their 3'-termini to said surface through terminal aminopropanol functions; and removing unbound oligonucleotides from the surface by washing with water.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
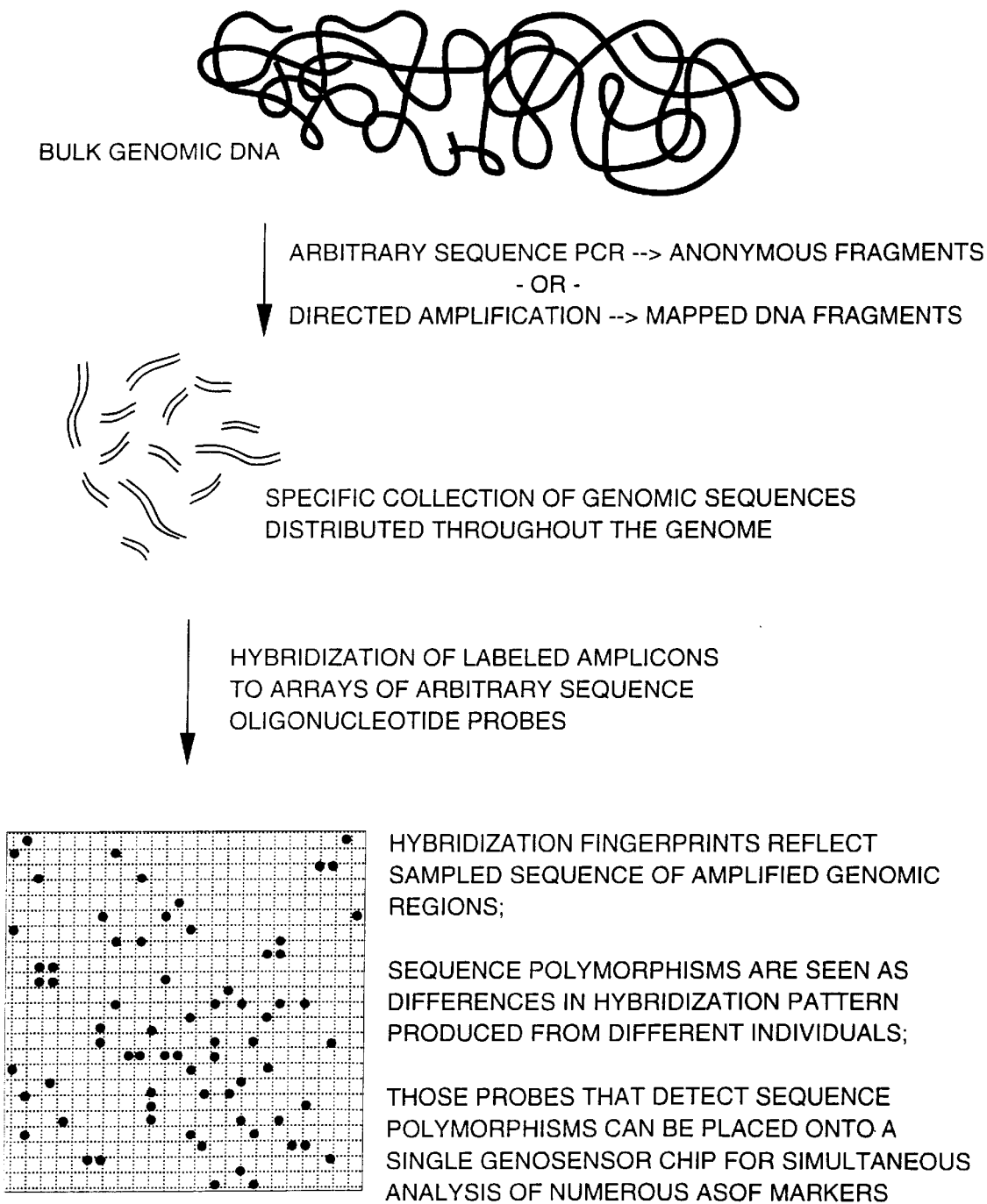
FIG. 1 illustrates graphically the method of arbitrary sequence oligonucleotide fingerprinting.

To understand the workings of the present invention, it is important to compare the expected throughput of arbitrary sequence oligonucleotide fingerprinting analysis with that of current DNA marker analysis techniques (RFLP, STRP and RAPD). For this comparison one can assume that a typical laboratory will conduct DNA marker analysis (by either genosensor-based or gel-based methods) on 200 samples per day. One can assume further that 200 arbitrary sequence oligonucleotide fingerprinting analyses, involving hybridization of arbitrary PCR products to an array of 200 miniature genosensor chips, can be achieved in equivalent time and space as a single analysis using 200 electrophoretic lanes. Additional assumptions include: when new polymorphic markers are being searched for, twenty tests are carried out per day with ten different individuals (200 samples total). In discovery of new RFLP markers, one assumes that each lane contains an average of 20 bands; the restriction site is 5 bases (average of 4-base and 6-base cutters). For STR and RAPD marker analysis one can assume that 50% of all lanes will reveal a polymorphism. For analysis of a known polymorphism, one should assume that each lane will test a single polymorphism in gel-based methods and that each genosensor containing a 50×50 array of probes will test an average of 1,000 polymorphic sites. Based on the above, throughput estimations are made for two cases: (i) discovery of new polymorphic markers; and (ii) subsequent analysis of known polymorphic markers. The following is predicted:

| # new polymorphisms discovered per day | | | |
|---|---|---|---|
| RFLP | STR | RAPD | ASOF |
| 10 | 10 | 10 | 500 |
| # known polymorphisms analyzed per day | | | |
| RFLP | STRP | RAPD | ASOF |
| 200 | 200 | 200 | 200,000 |

The above predictions suggest a fifty-fold increase in throughput for genosensor-based arbitrary sequence oligonucleotide fingerprinting marker analysis of the present invention compared with standard gel-based analyses, during the identification of new polymorphic markers. The increase in throughput for analysis of known polymorphisms is even more dramatic (1000-fold increase for arbitrary sequence oligonucleotide fingerprinting analysis compared with gel-based techniques). The present invention combines the throughput advantages for both DNA marker discovery and DNA marker screening (genotyping), both of which are important in genome analysis.

The present invention provides a method of detecting DNA sequence polymorphisms in a sample, comprising the steps of: amplifying a sample of genomic DNA using the polymerase chain reaction (PCR); labeling the amplified genomic subset; hybridizing the amplified genomic subset with a two-dimensional array of surface bound oligonucleotide probes of arbitrary sequence; and; detecting polymorphisms in the sample of genomic DNA by detecting changes in the quantitative hybridization fingerprint within the DNA probe array. Generally, the method of amplifying the genomic DNA in the technique of the present invention is selected from the group consisting of (1) PCR using individual short oligonucleotides (8 mer–12 mer) of arbitrary sequence; (2) PCR using mixtures of longer oligonucleotides, for example 100 13 mer–15 mer of arbitrary sequence; (3) PCR using at least one pair of specific primers targeted to at least one genomic region known to display a high degree of sequence polymorphism; and (4) PCR using a multiplicity of primer pairs targeted to specific genomic regions, for example, 20–100 sequence tagged sites (STSs). Generally, a person having ordinary skill in this art can detect polymorphisms in the sample of genomic DNA by detecting changes in the quantitative hybridization fingerprint within the DNA probe array (i.e., changes in the relative quantity of label at different sites) using such techniques as phosphorimager analysis, autoradiography and CCD camera image analysis.

The present invention also provides a method of oligonucleotide array fingerprinting for classification or identification of species in a biological sample, comprising the steps of: extracting DNA from the biological sample; conducting the polymerase chain reaction to prepare a set of DNA fragments corresponding to a subset of genomic sequences; labeling the amplified genomic subset; hybridizing the labeled fragments to arrays of oligonucleotides of arbitrary sequences; and making species classification or identification by comparing the hybridization fingerprint across the DNA probe array with a database of specific hybridization fingerprints previously determined to correspond to known species.

The present invention further provides a method of analyzing mixed populations of organisms in environmental samples by oligonucleotide array fingerprinting, comprising the steps of: extracting DNA from a sample of soil, water, or industrial process stream; conducting PCR to prepare DNA fragments corresponding to a subset of genomic sequences in the environmental sample; labeling the amplified fragments; hybridizing the labeled fragments to arrays of oligonucleotide probes of arbitrary sequences; and detecting differences in cellular populations between environmental samples, reflected by differences in the quantitative hybridization fingerprints across the oligonucleotide arrays.

The present invention in addition provides a method of analyzing patterns of gene expression, comprising the steps of: extracting RNA from a cellular sample; preparing DNA fragments representing expressed genes; labeling the DNA fragments; hybridizing the labeled fragments to arrays of oligonucleotide probes of arbitrary sequence; and detecting changes in gene expression from changes in the relative hybridization intensity at different positions across the DNA probe array. Generally, the method of preparing DNA fragments representing expressed genes is selected from the group consisting of reverse transcriptase polymerase chain reaction (RT-PCR) to prepare cDNA, PCR strategies to prepare subfractions of expressed sequences, as used in gel electrophoresis-based differential display analysis, and steps of PCR, restriction fragmentation, subtractive hybridization and gel electrophoresis, as used in representational difference analysis (RDA).

The present invention also provides a method of direct fingerprinting of complex genomes without DNA amplification, comprising the steps of: mixing genomic DNA extracted from a biological sample with at least one labeled oligonucleotide probe of arbitrary sequence and hybridizing the mixture with an array of arbitrary sequence capture probes, using conditions of temperature and ionic strength under which neither the labeled probe(s), nor capture probes alone will stably hybridize with the DNA target, but under which capture and labeled probes, when tandemly hybridized to a target strand to form a longer, contiguously base-stacked combined duplex region, will result in stable capture of the target strand; and comparing the hybridization fingerprint with genomic fingerprints obtained from different biological samples.

The present invention further provides a method of direct transcriptional profiling in a biological sample, comprising the steps of: mixing bulk messenger RNA extracted from the biological sample with at least one labeled oligonucleotide probe of arbitrary sequence and hybridizing the mixture with an array of arbitrary sequence capture probes, using conditions of temperature and ionic strength under which neither the labeled probe(s), nor capture probes alone will stably hybridize with the RNA target, but under which capture and labeled probes, when tandemly hybridized to a target strand to form a longer, contiguously base-stacked combined duplex region, will result in stable capture of the RNA transcript; and comparing the hybridization fingerprint with RNA fingerprints obtained from different biological samples.

The arbitrary sequence capture probes and labeled probes used in the tandem hybridization embodiment of direct nucleic acid fingerprinting are preferably of length 7–9 bases. Libraries of capture probes and labeled probes for nucleic acid fingerprinting can be conveniently maintained, to provide a universal resource for fingerprinting of any nucleic acid sample. Hybridization fingerprints of known genomes or associated with known physiological conditions can be archived in a database and queried for identity and similarity with newly acquired fingerprints. The oligonucleotide probes that are mixed with the nucleic acid sample in the tandem hybridization embodiments of arbitrary sequence oligonucleotide fingerprinting described above can b e labeled with a variety of tags, selected from the group consisting of: radioactive labels (32P, 33P, 35S), which can be introduced onto the 5'-end of synthetic oligonucleotides using polynucleotide kinase; fluorescent tags, which can be introduced into the probes during chemical synthesis of oligonucleotides (using fluorescent phosphoramidites), or chemically coupled with primary amine-derivatized oligonucleotides; and biotin, which can also be introduced into the probes during chemical synthesis of oligonucleotides. The simultaneous use of a multiplicity of fluorescent labels can greatly increase the information content of the hybridization fingerprint. The use of biotinylated probes has the advantage of enabling enzymatic signal amplification to produce fluorescent, chemiluminescent or colored products, through use of a variety of commercially available enzyme-conjugated streptavidin and substrates signal-generating substrates.

In the direct fingerprinting (tandem hybridization) embodiment of the present invention, designed for analysis of nucleic acid samples of high genetic complexity, the preferred hybridization substrate is channel glass or porous silicon (flowthrough genosensor), in which probes are immobilized within patches of densely arrayed channels of 1–10 micron diameter extending across a glass or silicon dioxide layer of typically 500 microns thick. The flowthrough genosensor has the following important advantages over the flat surface genosensor configuration, which enable the direct fingerprinting embodiments of the present invention: improved hybridization kinetics, detection sensitivity and dynamic range, due to greatly increased surface area per unit cross section; greatly improved hybridization of dilute nucleic acid solutions, which can be slowly flowed through the porous hybridization array; and ability to simultaneously analyze both strands of duplex DNA fragments (simply by heat-denaturing a dilute DNA sample prior to passing it through the flowthrough genosensor), without having to physically isolate the two strands prior to hybridization, as is typically required for hybridization on a flat surface.

In all embodiments of arbitrary sequence oligonucleotide fingerprinting of the present invention, hybridization is generally carried out as follows. Oligonucleotide arrays on glass are "prehybridized" by soaking for 1 hr at room temp. in a "blocking solution" followed by a brief water wash. A solution of 10–20 mM tripolyphosphate is an effective and economical blocking solution for minimizing the nonspecific binding of $^{32}$P-labeled target strands to glass slides. Target DNA (typically, PCR product) is dissolved in (or added to) hybridization buffer (either 6XSSC or 3.3M tetramethylammonium chloride in 50 mM Tris-HCl (pH 8), 2 mM EDTA, 0.1% SDS and 10% polyethylene glycol-8000) at a concentration of 10–50 fmol strands per microliter (10–50 nM). If the target strands are labeled with $^{32}$p, a minimum of 2,000 cpm per microliter is used in the hybridization mixture, and prior to addition of labeled DNA to the hybridization mixture, unincorporated label is removed by loading the DNA onto a Microcon-3 microconcentrator (Amicon, Beverly, Mass.) and washed three times with water. Furthermore, if PCR is used to amplify the target, the PCR product is processed with a Millipore (Bedford, Mass.) Ultrafree spin-filter (30,000 molecular weight cutoff) to remove excess PCR primers prior to hybridization. An aliquot of target DNA in hybridization buffer is pipetted onto the microscope slide (20 microliters for an array occupying ⅓ of the slide or 60 microliters for the entire slide) and covered with a glass cover slip. The slide is incubated at 6 deg C for 2 hr to overnight, then the slide is washed at room temperature for at least 1 hr with hybridization buffer without PEG. For hybridization of immobilized probes of different lengths, variations in the hybridization and temperature should be explored to optimize the hybridization with respect to signal intensity and mismatch discrimination. Hybridization of 12 mer arrays can be conveniently carried out at room temperature in the above hybridization buffer. If target strands are labeled with $^{32}$P, hybridization can generally be quantitated within a few minutes using a phosphorimager, although overnight exposure against X-ray film is adequate for autoradiographic detection.

The present invention in addition provides a method for preparation of oligonucleotide arrays for hybridization analysis of nucleic acid samples, comprising the steps of: chemical synthesis of oligonucleotide probes using the standard phosphoramidite method with 3'-Amino-Modifier C3 CPG solid phase support (available from Glen Research, Sterling, Va.), which generates the 3'-aminopropanol function upon cleavage of the oligonucleotide from the support; cleaning the glass surface to be used as hybridization support with at least one organic solvent (for example, acetone and ethanol), followed by drying at elevated temperature; dissolving the 3'-aminopropanol-derivatized oligonucleotides in water at a concentration of 10–20 micromolar; applying a small droplet of each oligonucleotide solution onto the clean, dry glass surface, typically in a volume of 10–1000 nanoliters, placed 0.5–2 millimeters apart on the surface; incubating at room temperature (typically 5–30 minutes), followed by washing with water, air drying and storing dessicated at room temperature.

The simplified attachment method described above is more convenient, faster and more reliable than the previous epoxysilane-amine attachment method, and also gives a lower background of nonspecific binding of target strands to the glass surface. Both attachment methods yield a similar probe attachment density within each hybridization site (approx. $10^{10}$ to $10^{11}$ molecules per square millimeter of glass surface).

Oligonucleotide probe solutions can be arrayed across the hybridization support manually, using a template below the glass surface to guide the positioning of each droplet, or alternatively, robotically, using an automated fluid dispensing instrument such a Hamilton Microlab 2200 system. The latter instrument is capable of reproducibly delivering droplets as small as ten nanoliters onto a glass surface, at 0.5–1 mm center-to-center spacing. In the preparation of extensive arrays of oligonucleotide using the simplified attachment procedure described above, covalent attachment occurs quickly, and even though the first droplets applied to the surface may dry before the last droplet is applied, the entire array may be held at room temperature until all droplets dry, then washed with water, yielding uniform attachment density across the array.

The following examples are given for the purpose of illustrating various embodiments of the invention and are not meant to limit the present invention in any fashion.

EXAMPLE 1

Rationale of ASOF

In several embodiments of the arbitrary sequence oligonucleotide fingerprinting technique provided herein, genomic DNA was subjected first to the polymerase chain reaction using a single short primer of arbitrary sequence or a mixture of longer arbitrary sequence primers. The amplified genomic subset was then labeled and hybridized with a two-dimensional array of a few hundred to a few thousand different surface-bound oligonucleotide probes. Polymorphisms that affect priming events during PCR or affect the binding of amplified target to surface-tethered probes are expected to induce changes in the hybridization fingerprint within the DNA probe array. The arbitrary sequence oligonucleotide fingerprinting method enables rapid identification of DNA markers followed by simultaneous screening of large numbers of markers. The arbitrary sequence oligonucleotide fingerprinting technique speeds the identification of genes and alleles relevant to m any disciplines, including pharmaceutical development, agricultural breeding programs, and forensics.

The concept of arbitrary sequence oligonucleotide fingerprinting is based, at least in part, on the following rationale. First, mutations at polymorphic sites will disrupt base pairing with PCR primers annealing at these sites and will interfere with hybridization of probes targeted to the polymorphic sites. Secondly, if a procedure of genomic sampling (using PCR to select specific sequences from the total genomic pool) is carried out which depends on base pairing, the population of PCR-sampled genomic sequences may be perturbed by DNA sequence polymorphisms. Third, the sequence variations (polymorphisms) represented in the set of amplified fragments are expected to be revealed by differences in the hybridization fingerprints produced from DNA of different individuals. Fourth, after numerous arbitrary sequence oligonucleotide fingerprinting experiments are carried out to identify specific oligonucleotides (within the array of arbitrary sequence probes) that are capable of revealing sequence polymorphism (ASOF markers) for each set of PCR fragments (produced by a specific PCR condition); then specific combinations of PCR and arrayed probes can be used simultaneously to analyze numerous ASOF markers. Finally, since the arbitrary sequence oligonucleotide fingerprinting method enables simultaneous analysis of numerous sequence polymorphisms, a person having ordinary skill in this art is able to screen for numerous polymorphic markers very rapidly.

The present invention discloses a two-step "sampling" procedure which is sensitive to sequence variation at either step (priming or hybridization) and the procedure simultaneously can examine thousands of sampled sequences for polymorphism. The technology involves two steps: First, a PCR reaction is carried out to specifically amplify a subfraction of the genome. Then the amplified DNA product is hybridized to a grid (e.g., 50×50 array) of end-linked oligonucleotide probes (a DNA probe array, or "genosensor") to yield a hybridization pattern. The nucleotide sequence of the PCR primers and support-bound probes are arbitrarily chosen (within certain selection rules) to insure wide "sampling" of genomic sequence polymorphisms and to enable uniform stability fo potential duplexes formed with probes of different sequence.

The use of short (e.g., 8 mer–10 mer) PCR primers with genomic DNA of plants or animals typically yields 50–100 bands in a gel electrophoretic assay, in the size range of a few hundred to a few thousand base pairs. The set of sampled genomic sequences typically represents a total of 50,000–100,000 base pairs of genomic DNA. When such a mixture produced from several individuals is analyzed by gel electrophoresis, one is lucky to find a single polymorphism (RAPD marker) with any given primer, seen as the presence or absence or shifting of a gel band. The present invention enables sequence variation within the amplified (sampled) genomic sequences to be detected more readily by hybridization of the entire mixture of fragments to an array of a few hundred to a few thousand oligonucleotide probes, yielding a complex "fingerprint" that will vary at one or more sites—by loss of hybridization signals, creation of new hybridization signals, or changes in relative signal intensity—compared with genomic DNA sampled from another individual). Thus, polymorphism within genomic targets of the arrayed DNA probes alters the hybridization "fingerprints." If mutations within genomic sequences complementary to the PCR primer disrupt the PCR priming ability (or create new priming opportunities) then the final hybridization pattern would also be perturbed. FIG. 1 is a schematic diagram summarizing the method of arbitrary sequence oligonucleotide fingerprinting in embodiments that utilize PCR to prepare specific collections of fragments.

EXAMPLE 2

Theoretical considerations

The ultimate implementation of ASOF technology is based upon experimentally optimized parameters of PCR primer and hybridization probe composition, length and number. However, it is useful to design starting conditions and to estimate the throughput of arbitrary sequence oligonucleotide fingerprinting marker analysis (compared with current technology), based on statistical predictions. The number and length of genomic fragments produced during arbitrary primer PCR can be experimentally determined and the appropriate set of oligonucleotide probes to be included in the hybridization array should to be specified. Assuming that the total length of amplified target sequence that is to be hybridized to the set of arrayed probes is 50,000 base pairs (100,000 bases), then for a probe of length, p, the average number of occurrences, n, of the probe within the target sequence is represented by $n=100,000/4^p$. From this value, one can predict the average number of hybridization signals that would be produced with a given composition (number and length) of DNA probe array. The following Table summarizes these calculations for DNA probes of various length:

TABLE I

| probe length | ave. no. of occurrences (p) within the amplified target | ave. number of hybridization signals for a given size of array | |
|---|---|---|---|
| | | 20 × 20 array | 50 × 50 array |
| 8mer | 1.53 | (610) | (3,815) |
| 9mer | 0.38 | 152 | 954 |
| 10mer | 0.10 | 38.1 | 238 |

From the above TABLE I, it appears that an array of 9 mer probes is a preferred embodiment of the arbitrary sequence oligonucleotide fingerprinting technique of the present invention. Further, the approximate number of ASOF markers that could be discovered in a single hybridization experiment (performed with DNA from ten individuals) using a 50×50 probe array must be considered. If an estimate of 0.005 for the average frequency of useful polymorphism per base pair (minor allele detectable in at 10% of individuals) is made, and it is assumed that 50% of single base changes is detectable at either the level of hybridization or priming, predictions can be made that hybridization of the products of arbitrary primer PCR (from ten individuals) to a 50×50 array of arbitrary sequence 9 mer probes will identify 20–25 polymorphisms.

EXAMPLE 3

PCR primers and amplification conditions

For untargeted ASOF analysis utilizing PCR to generate a subset of genomic fragments, primers of arbitrary sequence are used, within limits of the following criteria: (i) 55–65% [G+C] content; (ii) exclusion of sequences containing strong secondary structure; and (iii) exclusion of sequences corresponding to known repeated sequences in genomic DNA such as Alu, SINE and LINE. The arbitrary sequence PCR is carried out under the conditions such as those described by Caetano-Anolles (9–12) for maximizing the detection of polymorphism in the gel electrophoretic analysis of PCR products produced with arbitrary sequence oligonucleotides of length 8–10. Single primer PCR was conducted with DNA samples prepared from two unrelated individuals—designated CF01 and CF02. Each PCR reaction contained, in 100 μL volume: 40 pmol primer, 50 ng DNA, 2.5 U Taq polymerase, 200 μM each dNTP, and standard PCR buffer. The thermocycling program used was: 90° C. 1 second; ramp to 23° C. at 0.2° C./second; hold 23° C. 1 second; ramp to 90° C. at 0.6° C./second; repeat above cycle 34 times; hold at 4° C.

Figure 2A:
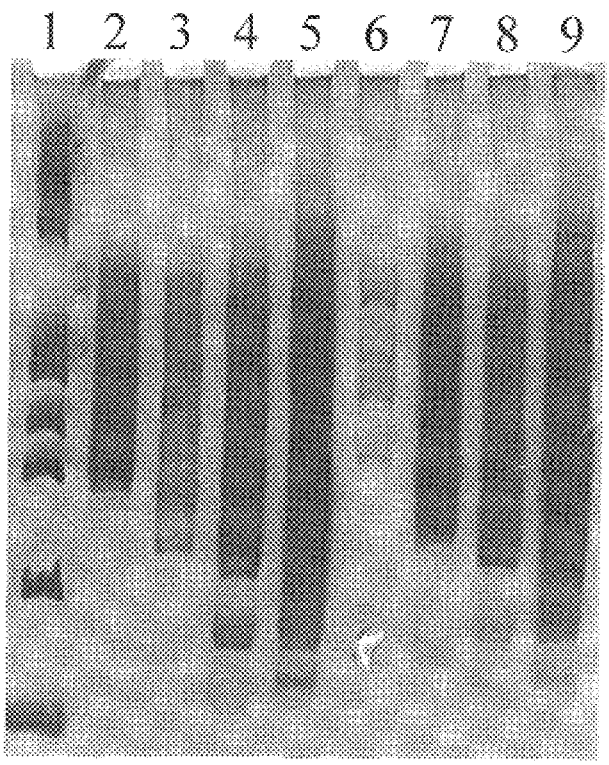
FIGS. 2A and B shows the gel electrophoretic display of silver-stained (FIG. 2A) and ethidium bromide-stained (FIG. 2B) gel of DNA fragments produced by single primer PCR.
Figure 2B:
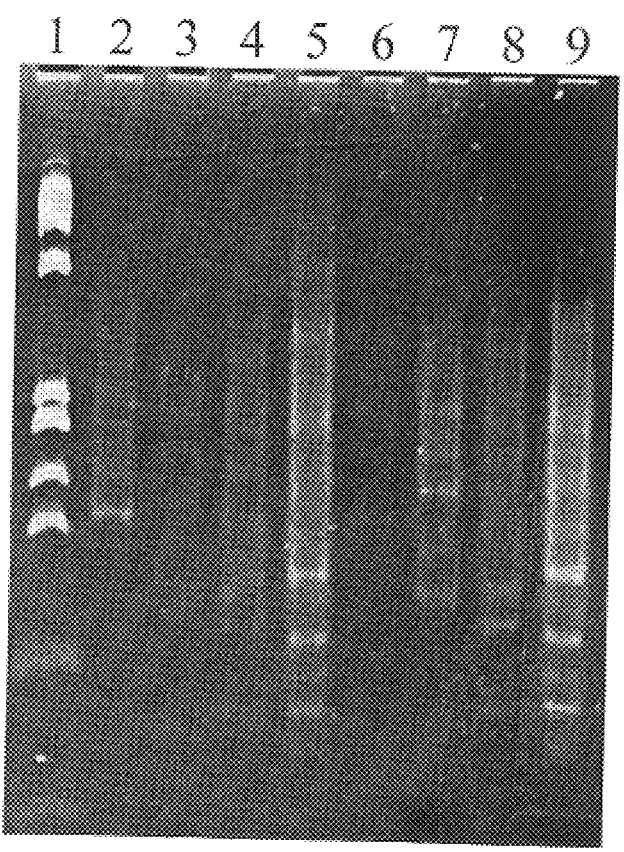

FIG. 2 displays silver-stained (FIG. 2A) and ethidium bromide-stained (FIG. 2B) gels of the PCR fragments, along with a marker lane consisting of products of φX174 RF DNA cleaved with HaeIII restriction enzyme. Table II shows the lanes illustrated by FIG. 1 that correspond to the following conditions:

TABLE II

| lane | DNA template | Primer and its sequence (5'->3') |
|---|---|---|
| 1 | marker lane | — |
| 2 | CF02 | Primer II: GTGTCGATC |
| 3 | CF02 | Primer IV: TGAGACGAC |
| 4 | CF02 | Primer VII: CGTGTAGFC |
| 5 | CF02 | Primer VIII: CGTGTACAG |
| 6 | CF01 | Primer II: GTGTCGATC |
| 7 | CF01 | Primer IV: TGAGACGAC |
| 8 | CF01 | Primer VII: CGTGTAGTC |
| 9 | CF01 | Primer VIII: CGTGTACAG |

EXAMPLE 4

PCR product fragmentation and labeling

The maximal DNA target length that can be captured efficiently by support-bound oligonucleotide probes has been shown. It was found that PCR fragments of at least 1000 bases can be hybridized to 9 mer oligonucleotides tethered to a glass surface. If it is necessary to fragment PCR products prior to hybridization to the genosensor array, sonication to produce random fragments of a few hundred base pairs in length is used. To enable quantitation of hybridization within the genosensor array using a phosphorimager system, PCR products are 5'-end labeled using polynucleotide kinase and [γ-$^{32}$P]ATP prior to hybridization. If additional detection sensitivity is required, target DNA is labeled by incorporation of [α-$^{32}$P]dNTPs in the PCR reactions.

EXAMPLE 5

Oligonucleotide array preparation

Figure 3:
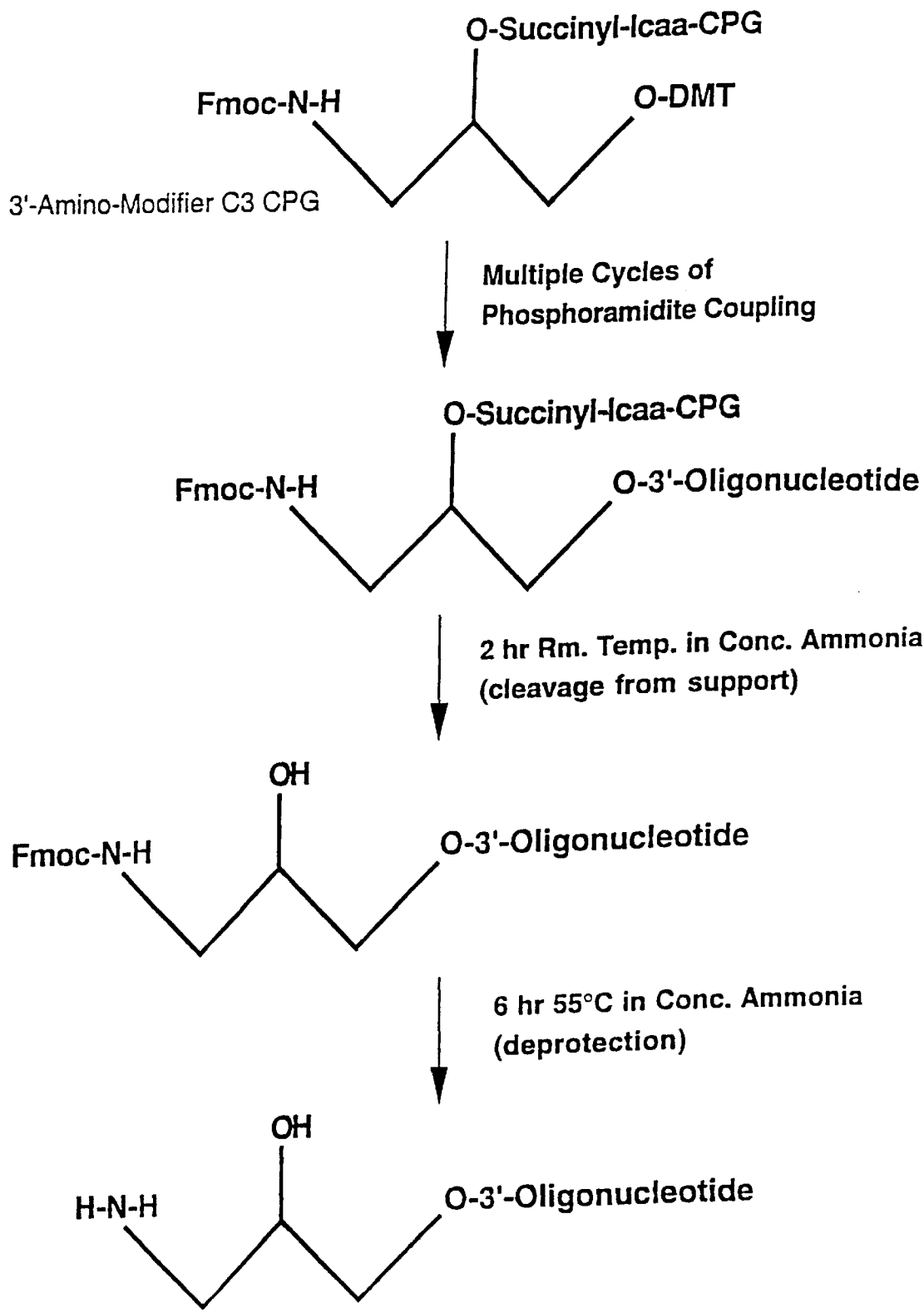
FIG. 3 shows the formation of 3'-aminopropanol-derived oligonucleotides.

Optimal conditions for preparation of oligonucleotide arrays and for carrying out discriminative hybridization have been defined. Preferred conditions are summarized as follows. Oligonucleotides are synthesized by the "porous wafer" segmented approach previously developed. (13 and 14). To enable simple probe immobilization on a glass surface it is preferable to synthesize the probes using 3'-Amino-Modifier C3 CPG (Glen Research) or the equivalent support from CloneTech, which yields terminal 3'-aminopropanol-derivatized oligonucleotides upon cleavage from the CPG support, as illustrated in FIG. 3.

A simple procedure has been devised for attachment of 3'-amino-propanol-oligonucleotide probes to underivattized glass surfaces. This procedure, which is suitable for the techniques of the present invention, involves the following steps: A glass plate is first cleaned by sonication in hexane and absolute ethanol for 10 minutes each. The slides are then incubated for 2–5 hours at 80° C. in a drying oven. Slides are stored desiccated under vacuum until used for probe attachment. Attachment of 3'-aminopropanol-derivatized oligonucleotides to the glass surface is then carried out as follows. A Hamilton Microlab 2200 robotic fluid dispensing system is used to place 3'-aminopropyl-derivatized oligonucleotides (10 μM solution in water) in 10–200 nl droplets onto the clean glass surface, at 0.5–2.0 mm center-to-center spacing. Slides are incubated at room temperature for 30 minutes, washed in water, then stored dry at room temperature. Quantitation of oligonucleotide attachment indicates that within each area of immobilized probe, oligonucleotide molecules are tethered to the glass with an average spacing of 50–100 Å using this procedure, corresponding to approximately $10^{10}$–$10^{11}$ probes/mm$^2$.

Figure 4:
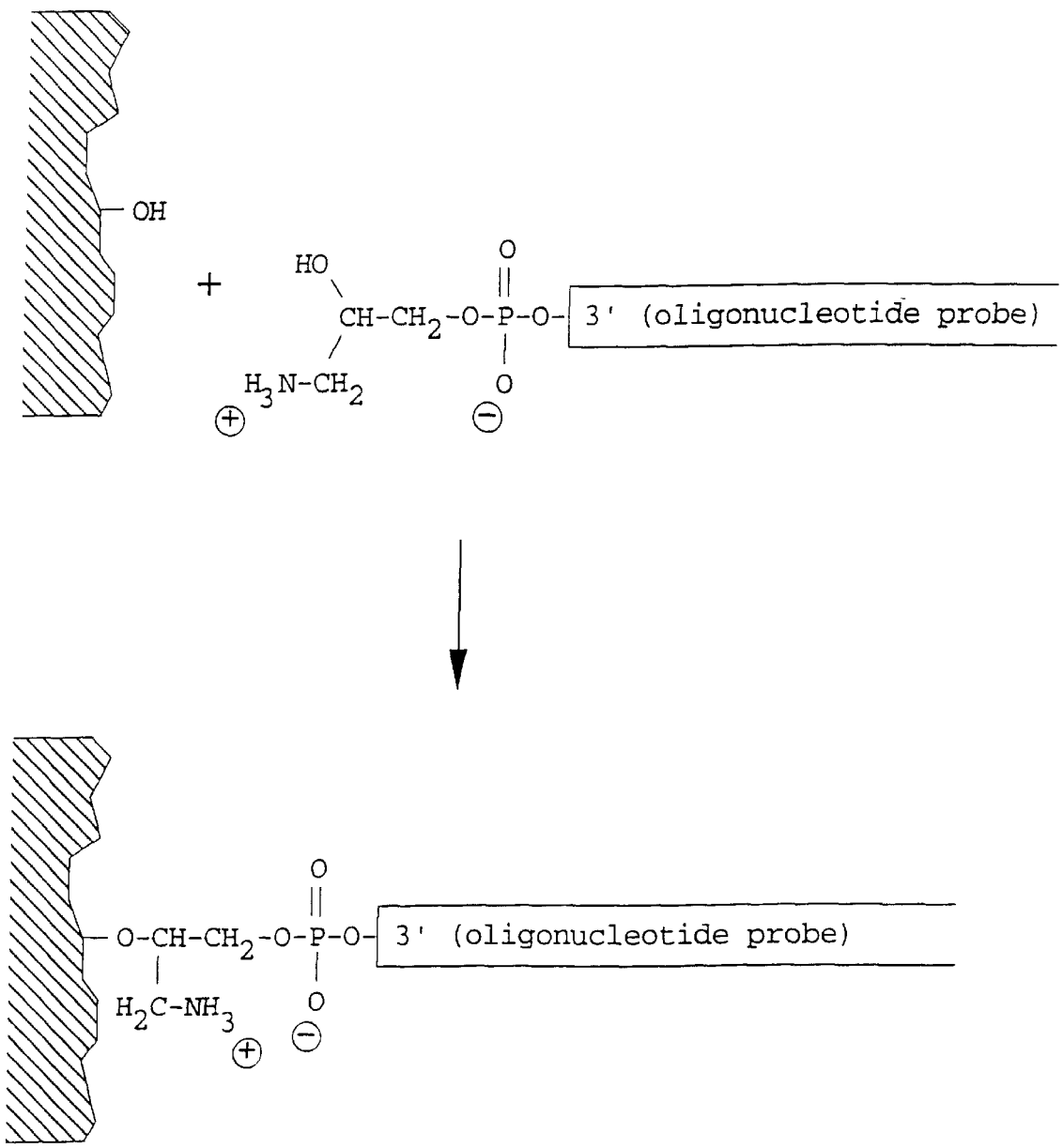
FIG. 4 depicts a scheme for covalent linkage of 3' aminopropanol oligonucleotides to plain glass surfaces.

FIG. 4 shows one synthesis scheme for covalent attachment. Formation of the ester linkage, rather than amide linkage, is supported by the finding that the linkage is stable in dilute acid (pH 4) but labile in dilute base (pH 10).

EXAMPLE 6

Hybridization Fingerprinting

Although some tailoring of hybridization conditions may be needed for the arbitrary sequence oligonucleotide fingerprinting technique, conditions identical to or very similar to those described below will achieve reproducible hybridization patterns. Oligonucleotide arrays on glass slides were pre-hybridized with 10 mM ATP at room temperature for 1 hour, then rinsed with hybridization solution consisting of 3.3 M tetramethylammonium chloride (TMAC), 50 mM Tris-HCl (pH 8.0), 2 mM EDTA, 0.1% SDS and 10% polyethylene glycol (PEG). $^{32}$P-labeled target DNA was dissolved in the hybridization solution at a concentration of 15–30 fmol/$\mu$l and a minimum of 1,000 cpm/$\mu$l, and 20 $\mu$l of this solution was applied to the area of the slide containing the attached probes. A cover slip was applied and the slide was incubated at 90° C. for 5 minutes, then 6° C. for at least 2 hours, then washed with hybridization solution without PEG room temperature for 2 hours.

Figure 5:
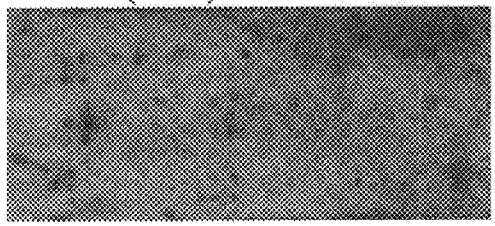
FIG. 5 shows the hybridization patterns obtained in the conduct of arbitrary sequence oligonucleotide fingerprinting using DNA extracted from three different individuals.
Figure 5:
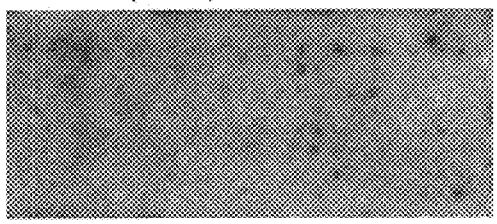
Figure 5:
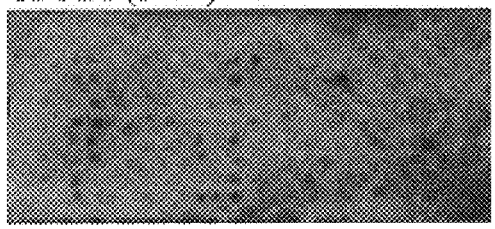
Figure 5:
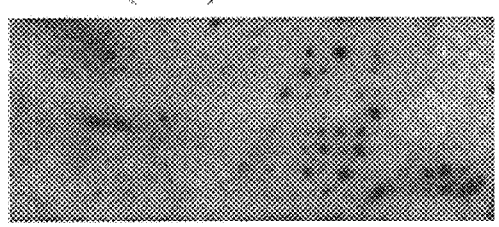
Figure 5:
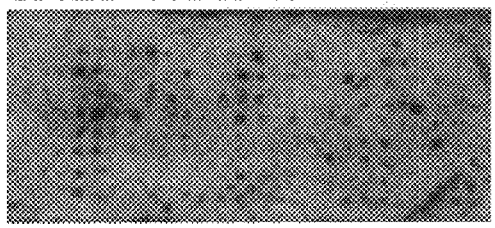
Figure 5:
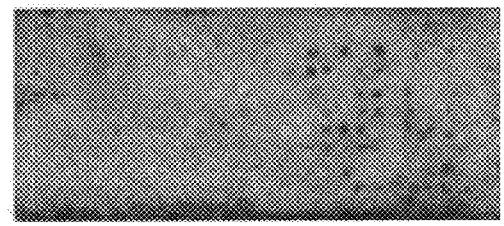
Figure 5:
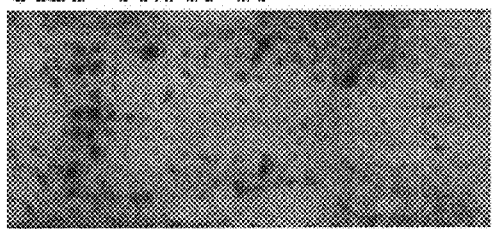
Figure 5:
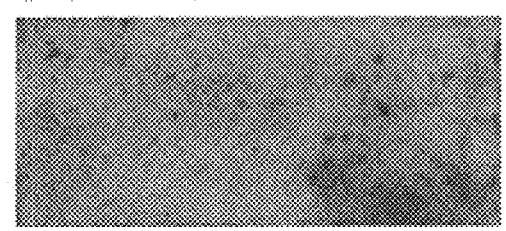

Representative hybridization fingerprints are shown in FIG. 5, for three different human DNA samples following PCR using a single primer. PCR was carried out using DNA from three different unrelated humans, designated CF01, CF02 and UK. The PCR reactions contained (in 100 $\mu$L) 100 ng template DNA, 200 $\mu$M each dNTP, 0.2 $\mu$M [5'-$^{32}$P] Primer I (5'-GTGTCGATG-3'), 5 U Taq polymerase, and standard PCR buffer. Prior to addition of template DNA and Taq polymerase, tubes were placed under a germicidal UV lamp and irradiated for 10 minutes. Tubes were held at 95° C. 5 minutes, then 30 cycles of thermocycling were conducted (90° C. 1 minute, 30° C. 1 minute, 72° C. 2 minutes), then tubes were brought to 95° C. for 5 minutes and another 2.5 U Taq polymerase was added and 30 more cycles of PCR were conducted as above. PCR mixtures were centrifuged through Ultrafree-30,000 spin filters (Millipore) to remove free primer, then suspended in hybridization buffer and hybridized to 9 mer arrays on microscope slides, as described in the previous paragraph. Two slides were used to obtain hybridization fingerprints using the above PCR products. Each slide contained 200 different 9 mers immobilized to the glass as described in Example 5. 9 mer probes were used in the oligonucleotide fingerprints of FIG. 5. One slide contained 9 mers of "box $^{15}/_{16}$" and the other "box $^{9}/_{10}$".

Close examination of the hybridization fingerprints of FIG. 5 resulting from different DNA samples reveals several apparent differences at specific locations within the array. Further experimentation, which can be readily carried out by one skilled in the art, is needed to identify the useful arbitrary sequence oligonucleotide fingerprinting markers and utilize them in high throughput marker analysis, as follows: the experiment is repeated using additional DNA samples for each single primer PCR (for example, a total of ten DNA samples, each analyzed five times). In addition, slides containing additional sets of arbitrary sequence probes is also used to obtain hybridization fingerprints. After the oligonucleotide probes that show reproducible detection of a polymorphism (hybridization present in some samples and absent in others or displaying reproducible differences in signal intensity) are identified for a given PCR primer (i.e., for each collection of PCR fragments that represents a specific subset of genomic sequences), the ASOF marker-specific probes is arrayed onto a slide for simultaneous analysis of all such markers detectable using the specific PCR reaction. Different sets of ASOF marker probes then is used for each PCR condition, to further increase the number of ASOF markers analyzed simultaneously.

EXAMPLE 7

Direct nucleic acid fingerprinting without PCR

The embodiments of the present invention of ASOF described in Examples 1, 2 and 6 employ PCR amplification to generate a subset of DNA sequences that can be fingerprinted by hybridization with an array of arbitrary sequence oligonucleotide probes. It is also possible to directly acquire hybridization fingerprints of DNA or RNA samples, without using DNA amplification to generate a subset of nucleic acid sequences of reduced genetic complexity. One way to achieve direct fingerprinting is to fragment the bulk nucleic acid sample (for example, by sonication, chemical cleavage or restriction enzyme digestion), label the fragments (for example, by use of polynucleotide kinase), then hybridize the entire mixture to an array of arbitrary sequence oligonucleotide probes of length greater than that used when PCR is used to generate a subset of target sequences. In the direct fingerprinting strategy the length of probes is chosen such that on average, each probe will hybridize with a maximum of one sequence within the entire collection of target strands present in the sample.

The appropriate probe length can be determined by trial and error, but can also be predicted using the relationship, $n = L/4^\wedge p$, where n represents the average number of occurrences of a probe of length p in a target sequence of total length L. For a sample of human genomic DNA containing six billion bases of sequence, the average number of occurrences of a 17-base probe in the entire genome is predicted to be 0.35; for a bacterial genome containing ten million bases of total sequence, each 12-base oligonucleotide probe of arbitrary sequence will occur on average, 0.60 times in the bacterial genome; and for a population of messenger RNA molecules of total length five million bases (example of transcribed sequences in a higher eukaryotic cell), the probability that an individual 12-base probe will yield a hybridization signal is predicted to be 0.30.

Using the appropriate probe length for directly fingerprinting a nucleic acid of a given genetic complexity, the hybridization fingerprint will preferably include hybridization signals at only ¼ to ⅔ of the hybridization sites. When the genetic complexity is high (millions or billions of bases of unique sequence in the sample) the hybridization fingerprint may be obtained using long hybridization times (hours to days) if the oligonucleotide probe array is attached to a flat surface such a a glass slide. The hybridization time can be shorted (minutes to hours) if the nucleic acid sample is slowly flowed through a channel glass or porous silicon hybridization substrate in which oligonucleotide probes are immobilized within patches of densely packed, straight, smooth channels, typically of diameter 1–10 micrometers, connecting the two faces of a glass or silicon wafer, typically 100–500 micrometers thick.

EXAMPLE 8

Direct nucleic acid fingerprinting using a tandem hybridization strategy

Figure 6:
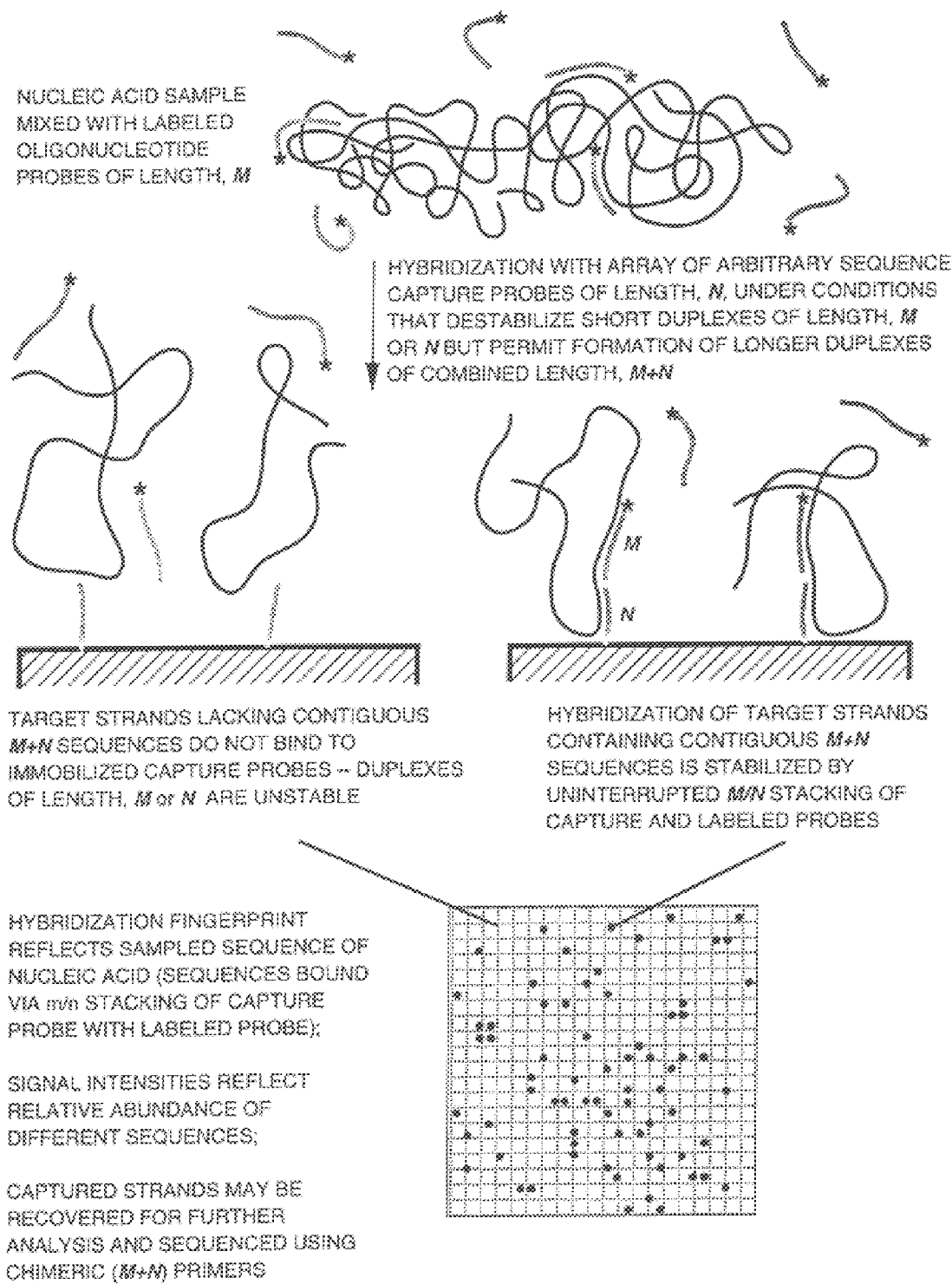
FIG. 6 illustrates the direct fingerprinting of complex nucleic acid samples using a tandem hybridization strategy.

Another strategy for achieving direct nucleic acid fingerprinting using an array of arbitrary sequence probes without DNA amplification is illustrated in FIG. 6. The bulk nucleic acid sample, extracted from a biological sample (for example, animal or plant tissue, cultured cells or soil sample), is first fragmented (for example, by chemical fragmentation, sonication or using restriction enzyme digestion) and mixed with a high molar excess of at least one oligonucleotide probe of length m that is labeled (for example, with a radioactive tag, a fluorescent tag or biotin). The mixture is then hybridized with an array of arbitrary sequence "capture probes" of length n. Hybridization conditions (temperature, ionic strength or concentration of denaturants such as formamide) are chosen such that neither the labeled probes, nor the capture probes, will form a stable duplex structure with the target strands, but duplexes of combined length m+n will be stable. Under these conditions a target strand will hybridize to the array only where a capture probe and labeled probe hybridize in tandem on the target strand, forming a contiguously base-stacked region of length m+n.

When unbound material is washed away with hybridization buffer, a hybridization fingerprint will be produced, which can be visualized and quantitated using a phosphorimager with $^{32}P$, $^{33}P$ or $^{35}S$ labels, or using a CCD camera and excitation light source with fluorescent tags. The quantitative hybridization fingerprint can be archived in a computer database and compared with fingerprints prepared from different samples. Mixtures of labeled probes, containing a multiplicity of distinguishable fluorescent tags, can be used to produce a "multicolor" hybridization fingerprint of greater information content.

The appropriate length of labeled and capture probes that are to be used in the tandem hybridization strategy of direct nucleic acid fingerprinting can be determined by trial and error, but can also be estimated using the relationship, n=L/4 to predict the average occurrence of probes within the entire target sequence, or the probability that a probe of length p will hybridize to a target sequence of length L. For example, in the case of a human genomic DNA sample of six billion bases, a 9-base capture probe is estimated to occur about 22,900 times (i.e., each 10 mer capture probe is predicted to hybridize with about 22,900 different target sequences). As explained above, however, stable hybridization will occur only if a labeled probe hybridizes in tandem with the capture probe on the target strand. If the tandem probe is also a 9 mer, the average occurrence of the probe in the 9-base target adjacent to the capture probe is estimated as $n=9/4^{\wedge}9$, or $3.43 \times 10^{\wedge}-5$. The combined occurrence of the tandem hybridization of capture and labeled probe is estimated as the product of the individual occurrences, which in the above example is 0.79. Upward adjustment of this estimate would be necessary if labeled probes could hybridize in tandem with the capture probe on either side of the capture probe, while downward adjustment would be needed if one considers that the analysis would preferably be targeted to euchromatin (unique sequences) within the genome. Nevertheless, it appears that capture and labeled probes approximately nine bases in length would be appropriate for use in the direct fingerprinting of human genomic DNA using the tandem hybridization approach, although actual optimal probe length can readily be determined experimentally. Using the same statistical approach, the appropriate length of capture and labeled probes for direct fingerprinting of a nucleic acid sample of ten million bases (for example, a bacterial genome or total expressed sequences in a higher eukaryote) is predicted to be about seven bases.

For direct fingerprinting of nucleic acid samples of high genetic complexity (for example, mammalian genomes or nucleic acids extracted from microbial populations) using the tandem hybridization strategy, the flowthrough genosensor configuration (utilizing a channel glass or porous silicon hybridization substrate) is greatly preferred, for the reasons given in Example 7. Furthermore, the nucleic acid strands bound to any given hybridization cell may be recovered from the support (for example, by elution with hot water) and used for further analysis (cloning, sequencing, PCR, etc.). An important additional feature of the tandem hybridization method of the present invention is that the combined sequence of tandemly hybridizing capture and labeled probes (m+n) can be used to define a sequence that can be synthesized and used for dideoxy sequencing or PCR amplification of the eluted nucleic acid strands.

EXAMPLE 9

Data collection and analysis

The hybridization intensities across the DNA probe array are measured using a Fuji phosphorimager. This instrument is 10–20 times more sensitive than standard X-ray film and can collect hybridization data across a total area of 20×40 cm. The Fuji phosphorimager system has resident software capable of quantitation of hybridization within the user-defined matrix and can store the data in digitized tabular form accessible to spreadsheet programs such as Excel. Alternatively, hybridization fingerprints can be analyzed by quantitative CCD camera imaging systems, when fluorescent or chemiluminescent labeling is used.

EXAMPLE 10

A simple, reliable procedure is used to link directly the 3'-aminopropanol-derivatized oligonucleotides to unmodified $SiO_2$ surfaces. The linkage is (i) stable in hot water, enabling multiple cycles of hybridization; (ii) stable in mild acid but labile in mild base (favoring the ester linkage over the amide linkage); (iii) not formed with 5'-hexylamine-derivatized oligonucleotides (primary amine alone is insufficient); (iv) inhibited by pretreatment of glass with propanolamine but not propylamine; and (v) blocked by acetylation of primary amine on oligonucleotide. The attachment reaction proceeds rapidly in aqueous solution at room temperature and gives a lower background of nonspecific binding of target DNA to the surface, compared with the previous epoxy-amine linkage method.

The following procedure is carried out for attachment of oligonucleotides to glass surfaces using the new direct coupling chemistry. Oligonucleotides are chemically synthesized using the 3'-Amino-Modifier C3 CPG support (Glen Research, Sterling, Va., cat. no. 20–2950) with the standard phosphoramidite chemistry (21). During cleavage of the oligonucleotides from the support the C3 amino group (actually a propanolamine function) is created at the 3'-end. Custom oligonucleotides with this 3'-propanolamine modification are available from Genosys Biotechnologies, Inc. (The Woodlands, Tex.). Oligonucleotides are dissolved in water at a concentration of 10–20 μM. Glass microscope slides are cleaned by rinsing with acetone and ethanol, and dried in an 80° C. oven. Droplets of oligonucleotide solution (typically 50–250 nL) are placed onto the clean, dry slide, incubated at room temperature for 5–15 min, then rinsed with water, air-dried and stored dessicated at room temperature. The attachment reaction occurs rapidly, and if some of the droplets dry during the application of all oligonucleotides in an array, the slide should be held at room temperature until all droplets dry before washing with water. (The reaction is apparently complete upon drying). If droplets are applied manually, the slide can be placed above a printed template to guide the placement of droplets. A commercially available robotic fluid dispensing system (Hamilton Micro- Lab 2200 system equipped with 21G needles and 50 μL syringes) is capable of robotically dispensing droplets as small as 10 nL onto a glass slide at 1 mm center-to-center spacing (Beattie et al., 1995a,b).

For hybridization of target strands to nonamer oligonucleotides attached to microscope slides the following standard procedure (Beattie et al., 1995a,b) can be used. Slides are "prehybridized" by soaking for 1 hr at room temp. in a "blocking solution" followed by a brief water wash. 10–20 mM tripolyphosphate has been found to be an effective and economical blocking solution for minimizing the nonspecific binding of $^{32}$P-labeled target strands to the glass slide (Beattie et al., 1995b). Target DNA (typically, PCR product) is dissolved in (or added to) hybridization buffer (either 6XSSC or 3.3M tetramethylammonium chloride in 50 mM Tris-HCl (pH 8), 2 mM EDTA, 0.1% SDS and 10% polyethylene glycol-8000) at a concentration of 10–50 fmol strands/μL (10–50 nM). If the target strands are labeled with $^{32}$O, a minimum of 2,000 cpm/μL is used in the hybridization mixture, and prior to addition of labeled DNA to the hybridization mixture, unincorporated label is removed by loading the DNA onto a Microcon-3 microconcentrator (Amicon, Beverly, Mass.) and washed three times with water. Furthermore, if PCR is used to amplify the target, the PCR product is processed with a Millipore (Bedford, Mass.) Ultrafree spin-filter (30,000 mol-wt cutoff) to remove excess PCR primers prior to hybridization. An aliquot of target DNA in hybridization buffer is pipetted onto the microscope slide (20 μL for an array occupying ⅓ of the slide or 60 μL for the entire slide) and covered with a glass cover slip. The slide is incubated at 6° C. for 2 hr to overnight, then the slide is washed at room temperature for at least 1 hr with hybridization buffer without PEG. For hybridization of immobilized probes of different lengths, variations in the hybridization and temperature should be explored to optimize the hybridization with respect to signal intensity and mismatch discrimination. Hybridization of 12 mer arrays can be conveniently carried out at room temperature in the above hybridization buffer. If target strands are labeled with $^{32}$P, hybridization can generally be quantitated within a few minutes using a phosphorimager (Beattie et al., 1995a,b), although overnight exposure against X-ray film is adequate for autoradiographic detection.

The present invention also provides a method of species, strain, subtype or gender identification, comprising the steps of: extracting genomic DNA from an organism, tissue or cells; amplifying a subset of genomic DNA sequences by a polymerase chain reaction using one or more oligonucleotide primers of arbitrary sequence; introducing at least one label into said amplified subset of genomic DNA; combining said amplified labeled subset of genomic DNA with a two-dimensional array of surface-bound oligonucleotide probes under hybridizing conditions to form a quantitative hybridization fingerprint for said genomic DNA; and identifying the species, strain, subtype or gender of the organism, by comparing said hybridization fingerprint with a database of hybridization fingerprints previously obtained from known species, strains, subtypes or genders.

The present invention additionally provides a method of analyzing and comparing mixed populations of organisms in biological or environmental samples, comprising the steps of: extracting DNA or RNA from a first biological or environmental sample; amplifying a first subset of nucleic acid sequences from said DNA or RNA extracted from said first biological or environmental sample by a polymerase chain reaction using one or more oligonucleotide primers of arbitrary sequence; introducing at least one label into said first subset of nucleic acid sequences; combining said first labeled, amplified subset of nucleic acid sequences with a two-dimensional array of surface-bound oligonucleotide probes under hybridizing conditions to form a first quantitative hybridization fingerprint for said first biological or environmental sample; extracting RNA or DNA from a second biological or environmental sample; amplifying a second subset of nucleic acid sequences from said DNA or RNA extracted from said second biological or environmental sample by a polymerase chain reaction using one or more oligonucleotide primers of arbitrary sequence; introducing at least one label into said second subset of nucleic acid sequences; combining said second labeled, amplified subset of nucleic acid sequences with said two-dimensional array of surface-bound oligonucleotide probes under hybridizing conditions to form a second quantitative hybridization fingerprint for said second biological or environmental sample; comparing said first quantitative hybridization fingerprint to said second quantitative hybridization fingerprint; and detecting differences in the population of organisms in said different biological or environmental samples, by detecting differences between said first quantitative hybridization fingerprint and said second quantitative hybridization fingerprint.

In another embodiment, the present invention provides a method of direct genomic fingerprinting of nucleic acids extracted from a biological or environmental sample, comprising the steps of: mixing genomic DNA or RNA extracted from a biological sample with a high molar excess of at least one labeled oligonucleotide probe of arbitrary sequence; hybridizing said mixture with an array of arbitrary sequence capture probes, using conditions of temperature and ionic strength under which neither the labeled probe(s), nor capture probes alone will stably hybridize with the DNA target, but under which capture and labeled probes, when tandemly hybridized to a target strand to form a longer, contiguously base-stacked combined duplex region, will result in stable capture of the target strand; and comparing the hybridization fingerprint with genomic fingerprints obtained from different biological samples. In one aspect, the arbitrary sequence oligonucleotide probe array is formed on a flat surface. The method may be performed wherein the arbitrary sequence oligonucleotide probe array is formed within a flowthrough layer of channel glass or porous silicon. Further, a wherein a multiplicity of labeled primers may be mixed with the nucleic acid extracted from a biological or environmental sample. If multiplicity of distinguishable labels are used, each may b e incorporated into a different labeled probe. Preferably, labeled probes and said capture probes are 8–10 bases in length.

The present invention also provides a method of directly analyzing and comparing mixed populations of organisms in biological or environmental samples, comprising the steps of: extracting DNA or RNA from a first biological or environmental sample; mixing said DNA or RNA extracted from said first biological or environmental sample with a high molar excess of at least one labeled oligonucleotide probe of arbitrary sequence; hybridizing said mixture derived from said first biological or environmental sample with an array of arbitrary sequence capture probes, using conditions of temperature and ionic strength under which neither the labeled probe(s), nor capture probes alone will stably hybridize with the DNA target, but under which capture and labeled probes, when tandemly hybridized to a target strand to form a longer, contiguously base-stacked combined duplex region, will result in stable capture of the target strand; obtaining a first quantitative hybridization fingerprint corresponding to said first biological or environmental sample; extracting DNA or RNA from a second biological or environmental sample; mixing said DNA or RNA extracted from said second biological or environmental sample with a high molar excess of at least one labeled oligonucleotide probe of arbitrary sequence; hybridizing said mixture derived from said second biological or environmental sample with an array of arbitrary sequence capture probes, using conditions of temperature and ionic strength under which neither the labeled probe(s), nor capture probes alone will stably hybridize with the DNA target, but under which capture and labeled probes, when tandemly hybridized to a target strand to form a longer, contiguously base-stacked combined duplex region, will result in stable capture of the target strand; obtaining a second quantitative hybridization fingerprint corresponding to said second biological or environmental sample; and comparing the quantitative hybridization fingerprint obtainded from said first biological or environmental sample with the quantitative hybridization fingerprint obtained from said second biological or environmental sample.

The present invention also provides a method of direct profiling of gene expression at the level of transcription, comprising the steps of: mixing bulk messenger RNA extracted from a biological sample with a high molar excess of at least one labeled oligonucleotide probe of arbitrary sequence; hybridizing said mixture with an array of arbitrary sequence capture probes, using conditions of temperature and ionic strength under which neither the labeled probe(s), nor capture probes alone will stably hybridize with the RNA target, but under which capture and labeled probes, when tandemly hybridized to a target strand to form a longer, contiguously base-stacked combined duplex region, will result in stable capture of the RNA transcript; and comparing said hybridization fingerprint with different hybridization fingerprints obtained from different biological samples. The arbitrary sequence oligonucleotide probe array may be formed on a flat surface. The arbitrary sequence oligonucleotide probe array can be formed within a flowthrough layer of channel glass or porous silicon. In one form multiplicity of labeled primers is mixed with the RNA sample. When a multiplicity of distinguishable labels are employed, each may be incorporated into a different labeled probe. The arbitrary sequence oligonucleotide probe array may be formed on a flat surface or formed within a flowthrough layer of channel glass or porous silicon. Preferably, the labeled probes and said capture probes are of length 6–8 bases.

Also provided is a method for directly analyzing and comparing nucleic acid samples of high genetic complexity, comprising the steps of: extracting DNA or RNA from a biological sample; adding at least one labeled oligonucleotide probe of arbitrary sequence to the extracted nucleic acid and hybridizing the mixture with an array of arbitrary sequence capture probes, using conditions of temperature and ionic strength under which neither the labeled probe(s), nor capture probes alone will stably hybridize with the target strands, but under which capture and labeled probes, when tandemly hybridized to a target strand to form a longer, contiguously base-stacked combined duplex region, will result in stable capture of the target strand; comparing the hybridization fingerprint with fingerprints obtained from different biological samples; eluting bound target strands from any desired hybridization cell in the array, by applying a denaturant solution to the desired location in the array; and further analyzing said eluted target strands, using the combined sequence of the capture and labeled probes to define a longer primer for PCR amplification or dideoxy sequencing.

The following references were cited herein:
1. Botstein, D., et al., Am. J. Hum. Genet. 3 2:314–331, (1980)
2. Nakamura, Y. et al., Science 235:1616–1622, (1987).
3. Jacob, H. J., et al., Cell 67:213–221, (1991).
4. Tautz, D., Nucl. Acids Res. 17:6463–6471, (1989).
5. Weber, J. L. et al., Am. J. Hum. Genet. 44:388–396, (1989).
6. Williams, J.G.K., et al., Nuci. Acids Res. 18:6531–6535, (1990).
7. Welsh, J. et al., Nucl. Acids Res. 18:7213–7218, (1991).
8. Dellaporta, S. L., et al., Plant Mol. Biol. Rep. 1:19–21, (1983).
9. Caetano-Anolles, G., et al., Mol. Gen. Genet. 235:157–165, (1992).
10. Caetano-Anolles, G. et al., Appl. Biochem. Biotechnol. 42:189–200, (1993).
11. Caetano-Anolles, G., PCR Meth. Applic. 3:85–94, (1993).
12. Caetano-Anolles, G., et al., Mol. Gen. Genet. 241:57–64, (1993).
13. Beattie, K. L., et al., Biotechnol. Appl. Biochem. 10:510–521, (1988).
14. Beattie, K. L. et al., Nature 352:548–549, (1991).
15. Parkam, M., et al., Biochem. Biophys. Res. Commun. 1: 1–6, (1978).
16. Lund, V., et al., Nucl. Acids Res. 1 6: 10861–10880, (1988)
17. Drmanac, R., et al., DNA Cell Biol. 9:527–534, 1990.
18. Beattie, K. L., et al, Clin. Chem, 41:700–706 (1995a).
19. Beattie, W. G., et al., Nucl Acids Res., submitted (1996b).
20. Beattie, W. G., et al., Molec Biotech, 4:213–225 (1995b).
21. Matteucci and Caruthers, J Am Chem Soc 103:3185–91 (1981).

What is claimed is:

1. A method of detecting sequence polymorphisms between samples of genomic DNA, comprising the steps of:
amplifying a first subset of genomic DNA sequences of genetic cqmplexity (total length of nonrepeating sequence) L from genomic DNA extracted from a first individual by a polymerase chain reaction using one or more oligonucleotide primers of arbitrary sequence;
introducing at least one label into said first amplified subset of genomic DNA sequences;
selecting a set of arbitrary sequence oligonucleotide probes of length p, such that the average number of occurrences, n, of each oligonucleotide probe of length p within said amplified subset of genomic DNA sequences of genetic complexity L, is no more than about one, as predicted from the formula, $n=L/4^p$;
preparing a two-dimensional oligonucleotide array comprising said set of arbitrary sequence oligonucleotide probes of length about p, immobilized onto a surface;
combining said first amplified subset of genomic DNA sequences with said two-dimensional oligonucleotide array under hybridizing conditions to form a first quantitative hybridization fingerprint for said first subset of genomic DNA sequences;
amplifying a second subset of genomic DNA sequences from genomic DNA extracted from a second individual by a polymerase chain reaction using said one or more oligonucleotide primers of arbitrary sequence;
introducing at least one label into said second amplified subset of genomic DNA;
combining said second amplified subset of genomic DNA with said two-dimensional array of surface-bound oligonucleotide probes of arbitrary sequence under hybridizing conditions to form a second quantitative hybridization fingerprint for said subset of genomic DNA sequences;

comparing said first quantitative hybridization fingerprint to said second quantitative hybridization fingerprint; and detecting sequence polymorphisms in said samples of genomic DNA by detecting differences between said first quantitative hybridization fingerprint and said second quantitative hybridization fingerprint.

2. The method of claim 1, wherein said one or more oligonucleotide primers of arbitrary sequence has a length of 8 to 10 nucleotides.

3. The method of claim 1, wherein said label is introduced by a method selected from the group consisting of incorporating labeled substrate in the PCR reaction and labeling the PCR fragments.

4. The method of claim 1, wherein said one or more oligonucleotide primers of arbitrary sequence has a G+C content of 55–65%.

5. The method of claim 1, wherein said one or more oligonucleotide primers of arbitrary sequence does not have a secondary structure.

6. The method of claim 1, wherein said one or more oligonucleotide primers of arbitrary sequence does not have sequences corresponding to Alu, LINE, SINE or other sequence elements that are repeated many times throughout the genome.

7. The method of claim 1, wherein the number of different oligonucleotide probes of arbitrary sequence arrayed on the surface is at least 100.

8. The method of claim 1, wherein the number of different oligonucleotide probes of arbitrary sequence arrayed on the surface is at least 1000.

9. A method of detecting sequence polymorphisms in a genomic DNA sample, comprising the steps of:

amplifying a first subset of genomic DNA sequences of genetic complexity L, from genomic DNA extracted from a first individual by a polymerase chain reaction using a multiplicity of defined sequence oligonucleotide primer pairs directed toward a corresponding multiplicity of known genomic regions;

labeling said first amplified subset of genomic DNA;

selecting a set of arbitrary sequence oligonucleotide probes of length p, such that the average number of occurrences, n, of each oligonucleotide probe of length p within said amplified subset of genomic DNA sequences of genetic complexity L, is no more than about one, as predicted from the formula, $n=L/4P$;

preparing a two-dimensional oligonucleotide array comprising said set of arbitrary sequence oligonucleotide probes of length p, immobilized onto a surface;

combining said first amplified subset of genomic DNA with a two-dimensional array of surface-bound oligonucleotide probes of arbitrary sequence under hybridizing conditions to form a first quantitative hybridization fingerprint for said first subset of genomic DNA sequences;

amplifying a second subset of genomic DNA sequences from genomic DNA extracted from a second individual by a polymerase chain reaction using said multiplicity of defined sequence oligonucleotide primer pairs directed toward a corresponding multiplicity of known genomic regions;

labeling said second amplified subset of genomic DNA;

combining said second amplified subset of genomic DNA sequences with said two-dimensional array of surface-bound oligonucleotide probes under hybridizing conditions to form a second quantitative hybridization fingerprint for said subset of genomic DNA sequences;

comparing said first quantitative hybridization fingerprint to said second quantitative hybridization fingerprint; and detecting polymorphisms in said samples of genomic DNA by detecting differences between said first quantitative hybridization fingerprint and said second quantitative hybridization fingerprint.

10. A method for profiling of gene expression at the level of transcription, comprising the steps of:

extracting RNA from a biological sample;

conducting reverse transcriptase-arbitrary primer PCR to amplify subsets of expressed sequences;

labeling said amplified subsets of expressed sequences from said biological sample;

combining said labeled amplified subset of expressed sequences with two-dimensional arrays of surface-bound arbitrary sequence oligonucleotide probes of various lengths ranging from about 7 bases to about 11 bases, under hybridizing conditions to produce a quantitative hybridization fingerprint for each length of probe;

detecting differences in gene expression by comparing said quantitative hybridization fingerprint with quantitative hybridization fingerprints obtained from a other experiments performed for other biological samples.

11. A method of species, strain, subtype or gender identification, comprising the steps of:

extracting genomic DNA from an organism, tissue or cells;

amplifying a subset of genomic DNA sequences of genetic complexity L from genomic DNA extracted from said organism, tissues, or cells by a polymerase chain reaction using one or more oligonucleotide primers of arbitrary sequence;

introducing at least one label into said amplified subset of genomic DNA sequences;

selecting a set of arbitrary sequence oligonucleotide probes of length p, such that the average number of occurrences, n, of each oligonucleotide probe of length p within said amplified subset of genomic DNA sequences of genetic complexity L, is no more than about one, as predicted from the formula, $n=L/4^P$ preparing a two-dimensional oligonucleotide array comprising said set of arbitrary sequence oligonucleotide probes of length p, immobilized onto a surface;

combining said amplified labeled subset of genomic DNA with said two-dimensional array of surface-bound oligonucleotide probes of arbitrary sequence;

measuring the hybridization signal at each array element to obtain a quantitative hybridization fingerprint which reflects the genomic DNA sequence from the organism; and identifying the species, strain, subtype or gender of the organism, by comparing said hybridization fingerprint with a database of quantitative hybridization fingerprints previously obtained from known species, strains, subtypes or genders.

12. A method of analyzing and comparing mixed populations of organisms in biological or environmental samples, comprising the steps of:

extracting DNA or RNA from a first biological or environmental sample;

amplifying a first subset of nucleic acid sequences from said DNA or RNA extracted from said first biological or environmental sample by a polymerase chain reaction using one or more oligonucleotide primers of arbitrary sequence;

introducing at least one label into said first subset of nucleic acid sequences;

combining said first labeled, amplified subset of nucleic acid sequences with a two-dimensional array of surface-bound arbitrary sequence oligonucleotide probes of appropriate length known to yield a hybridization fingerprint in which about ⅕ to about ½ of the array elements contain detectable hybridization signal to form a first quantitative hybridization fingerprint for said first biological or environmental sample;

extracting RNA or DNA from a second biological or environmental sample;

amplifying a second subset of nucleic acid sequences from said DNA or RNA extracted from said second biological or environmental sample by a polymerase chain reaction using one or more oligonucleotide primers of arbitrary sequence;

introducing at least one label into said second subset of nucleic acid sequences;

combining said second labeled, amplified subset of nucleic acid sequences with said two-dimensional, array of surface-bound oligonucleotide probes under hybridizing conditions to form a second quantitative hybridization fingerprint for said second biological or environmental sample;

comparing said first quantitative hybridization fingerprint to said second quantitative hybridization fingerprint; and detecting differences in the population of organisms in said different biological or environmental samples, by detecting differences between said first quantitative hybridization fingerprint and said second quantitative hybridization fingerprint.

13. A method of direct fingerprinting of genomic DNA extracted from a biological or environmental samples, comprising the steps of:

mixing said genomic DNA extracted from said biological samples with a molar excess of at least one labeled oligonucleotide probe of arbitrary sequence;

hybridizing said mixture with an array of surface bound oligonucleotide capture probes of arbitrary sequence, the lengths of said capture probes selected to yield a hybridization fingerprint in which about ⅕ to about ½ of the array elements contain significant hybridization signal using conditions of temperature and ionic strength under which neither the labeled probe(s), nor capture probes alone will stably hybridize with the genomic DNA target, but under which capture and labeled probes, when tandemly hybridized to a target strand to form a longer, contiguously base-stacked combined duplex region, will result in stable capture of the target strand; and comparing the hybridization fingerprint with genomic fingerprints obtained from different biological samples.

14. The method of claim 13, wherein the array of surface bound oligonucleotide capture probes of arbitrary sequence is formed on a flat surface.

15. The method of claim 13 wherein the array of surface bound oligonucleotide capture probes of arbitrary sequence is formed within a flowthrough layer of channel glass or porous silicon.

16. The method of claim 13, wherein a multiplicity of labeled probes is mixed with the genomic DNA extracted from said biological or environmental sample.

17. The method of claim 13, wherein a multiplicity of distinguishable labels are used, each incorporated into a different labeled probe.

18. The method of claim 13, wherein said labeled probes and said capture probes are 8–10 bases in length.

19. A method of directly analyzing and comparing profiles of gene expression at the level of transcription, comprising the steps of:

mixing RNA extracted from a biological sample with a molar excess of at least one labeled oligonucleotide probe of arbitrary sequence;

hybridizing said mixture with an array of surface bound oligonucleotide capture probes of arbitrary sequence the length of said capture probes selected to yield a hybridization fingerprint in which about ⅕ to about ½ of the array elements contain significant hybridization signal using conditions of temperature and ionic strength under which neither the labeled probe(s), nor capture probes alone will stably hybridize with the RNA target, but under which capture and labeled probes, when tandemly hybridized to a target strand to form a longer, contiguously base-stacked combined duplex region, will result in stable capture of the RNA transcript; and measuring the hybridization signal at each array element to obtain a quantitative hybridization fingerprint which reflects the relative abundance of different gene transcripts in the RNA sample, comprising the profile of gene expression; and comparing said hybridization fingerprint with other hybridization fingerprints obtained from other biological samples, wherein the other quantitative hybridization fingerprints represent known profiles of gene expression.

* * * * *